United States Patent [19]

MacLeay et al.

[11] 4,243,821

[45] Jan. 6, 1981

[54] PROCESS FOR THE PREPARATION OF SYMMETRICAL DICUMYL PEROXIDES

[75] Inventors: Ronald E. MacLeay, Williamsville; Robert T. Kazmierczak, Cheektowaga, both of N.Y.

[73] Assignee: Pennwalt Corporation, Philadelphia, Pa.

[21] Appl. No.: 75,356

[22] Filed: Sep. 13, 1979

[51] Int. Cl.$^3$ ............................................. C07C 179/06
[52] U.S. Cl. ..................................................... 568/561
[58] Field of Search ........................ 568/558, 560, 561

[56] References Cited

U.S. PATENT DOCUMENTS

| | | | |
|---|---|---|---|
| 3,054,826 | 9/1969 | Weissermel et al. | 568/558 |
| 3,267,066 | 8/1966 | Tijssen | 568/558 |
| 3,458,557 | 7/1965 | Milas | 568/558 |
| 3,829,503 | 8/1974 | Kato et al. | 568/558 |
| 4,133,835 | 1/1979 | Bafford et al. | 568/558 |

FOREIGN PATENT DOCUMENTS

| | | | |
|---|---|---|---|
| 1216305 | 12/1966 | Fed. Rep. of Germany | 568/561 |
| 2035127 | 6/1973 | Fed. Rep. of Germany | 568/561 |
| 1243313 | 8/1971 | United Kingdom | 568/560 |

OTHER PUBLICATIONS

Tobolsky, "Organic Peroxides", Interscience Pub., 1954, N.Y.

*Primary Examiner*—Werren B. Lone

[57] ABSTRACT

An olefin such as α-methylstyrene or a substituted α-methylstyrene, wherein the substituent is on the phenyl ring, a t-cumyl halide corresponding to the hydrohalogenated olefin or a substituted t-cumyl chloride and hydrogen peroxide are reacted under relatively non-aqueous conditions, in the absence of a free acid and in the presence of a phenol, to obtain a symmetrical dicumyl (or substituted dicumyl) peroxide which is useful as cross-linking agents for polyethylene and elastomers.

5 Claims, No Drawings

PROCESS FOR THE PREPARATION OF SYMMETRICAL DICUMYL PEROXIDES

BACKGROUND OF THE INVENTION

1. Field of the Invention

This invention relates to an improved process for the preparation of symmetrical dicumyl peroxide or substituted dicumyl peroxides wherein the substituents are inert substituents in the phenyl ring of the t-cumyl group. More particularly, the invention relates to an improvement in the process of preparing symmetrical dicumyl peroxides by reacting a t-cumyl halide with hydrogen peroxide in the presence of an olefin corresponding to the dehydrohalogenated t-cumyl halide and a phenol catalyst.

2. Description of the Prior Art

The preparation of aralkyl and alkyl peroxides is well known in the prior art and can best be summarized under four major methods of preparation.

(1) The acid-catalyzed condensation of a hydroperoxide with an alcohol.

(2) The acid-catalyzed addition of a hydroperoxide to an olefin.

(3) The displacement reaction between an alkali metal salt of a hydroperoxide and an alkyl halide.

(4) The displacement reaction between a hydroperoxide or hydrogen peroxide and an alkyl halide in the presence of an acid acceptor.

The fourth method is the only method relevant to this invention. The other methods and their short-comings in the preparation of cumyl peroxides are thoroughly discussed in U.S. Pat. No. 4,133,835 (Bafford).

Tijssen (U.S. Pat. No. 3,267,066) in Example IV prepared dicumyl peroxide in 66% yield by reacting hydrogen chloride, α-methylstyrene, and 70% cumene hydroperoxide for 5 hours at 40° C.

Kato et al. (Auslegeschrift No. 2,035,127) published a process for preparing t-cumyl type peroxides by reacting a tertiary hydroperoxide with an aralkyl halide, such as t-cumyl chloride, at 0°–80° C. in the presence of an acid binding agent such as a t-alcohol or an aliphatic olefin. In this process the hydroperoxide reacts with the aralkyl halide to form the peroxide; the HCl generated is taken up by the acid binding agent. There is no regeneration of the t-cumyl chloride.

Bafford (U.S. Pat. No. 4,133,835) disclosed a process which consisted of adding an aliphatic or cycloaliphatic hydroperoxide to an olefin such as a 1-aromatic-1-substituted ethylene and an aralkyl halide corresponding to the hydrohalogenated ethylene under essentially anhydrous conditions in the absence of a free acid, at a temperature below the decomposition temperature of the halide. The main object of his invention was to provide a process for the preparation of certain peroxides, especially acid-sensitive peroxides, by a procedure that does not use a free-acid catalyst. The process is similar to that of Kato's except Bafford uses the 1-aromatic-1-substituted ethylene as the acid binding agent. By doing this, aralkyl halide is regenerated. Consequently, a low concentration of the aralkyl halide in the olefin can be used; the reaction becomes less acid sensitive and the economics are much better.

Kloosterman et al. (Auslegeschrift No. 1,216,305) describe a process for the preparation of dicumyl peroxide and its ring chlorinated derivatives by the reaction of t-cumyl chloride or its ring chlorinated derivatives with an aqueous solution of hydrogen peroxide at 0°–40° C. in the presence of an acid binding medium so that the pH of the reaction mixture stays between −1 and 2.5 on a glass/kalomel electrode. In a stronger acid medium, decomposition exotherms were reported to occur. A mole ratio of t-cumyl chloride to hydrogen peroxide of 1:0.5 to 1:0.8 were used in this system. The anhydrous basic acid binding agents, such as $Na_2CO_3$, $K_2CO_3$ or $NH_3$, had to be added portionwise throughout the reaction so that the pH held between −1 and 2.5.

The process of the present invention has economic advantages over the prior art processes that used cumene hydroperoxide. First of all there is a considerable economic advantage in substituting hydrogen peroxide for cumene hydroperoxide. In addition the present process can be run at a lower temperature and much faster than the reactions of the prior art; therefore a much larger amount of dicumyl peroxide can be made in the same equipment in the same period of time. There is very little buildup of cumene hydroperoxide during the reaction and no apparent breakdown into phenol and acetone. In the prior art processes, this is a very serious problem and approximately 40% of the cumene hydroperoxide decomposes into phenol, acetone and other impurities which contaminate the final product. Since there is no cumene hydroperoxide breakdown, the catalytic amount of phenol present is easily removed, regenerated and recycled. The regenerated phenol is not contaminated with cumene hydroperoxide decomposition products. The excess α-methylstyrene can be stripped off from the dicumyl peroxide and readily recycled.

When cumene hydroperoxide is used, the α-methylstyrene is contaminated with cumene since the commercial grades of cumene hydroperoxide contain a considerable amount of cumene. The cumene would have to be separated from the α-methylstyrene before the α-methylstyrene could be reused. The reaction is much easier to control and the heat generated during the reaction is less than the prior art reactions because there is no cumene hydroperoxide decomposition occurring. Since the bulk of the reaction occurs very readily, the instant process has been adapted to a continuous process.

Kloosterman (Auslegeschrift No. 1,216,305) was the only inventor in the prior art who reacted hydrogen peroxide with a t-cumyl halide. He used a 50% excess of hydrogen peroxide over the t-cumyl halide and he used weak inorganic bases as the acid binding agents. Although the process worked, the procedure is cumbersome, the reaction period is quite long and he does not regenerate his reactive ingredient, the t-cumyl halide. Kloosterman's reactions took 8 hours to complete while we can run our reactions in anywhere from ½ hour to 1½ hours depending on the reaction conditions. Kloosterman required very tight pH control during his reactions. In most cases he added insoluble weak inorganic bases to the reaction mixture to neutralize the HCl generated in the reaction. This made stirring very difficult and built up the volume in the reactor, decreasing the amount of product that can be made in a given reactor volume. In the instant process α-methylstyrene prevents formation of HCl by regenerating our active ingredient, the t-cumyl chloride. It allows use of a minimal amount of t-cumyl chloride in the reaction and an increase or decrease in the rate of reaction by increasing or decreasing the t-cumyl chloride concentration and- /or the phenol concentration. Kloosterman makes no mention of any catalysts for his process. The effect of the phenol catalyst in the instant process is clearly shown in Example IIB where little dicumyl peroxide was formed in the absence of phenol.

STATEMENT OF INVENTION

This invention is directed to an improvement in the process of preparing symmetrical dicumyl peroxides comprising reacting an aqueous solution of hydrogen peroxide, an olefin such as α-methylstyrene or a substituted α-methylstyrene and a t-cumyl halide corresponding to the hydrohalogenated α-methylstyrene or substituted α-methylstyrene such as t-cumyl chloride (or bromide) or a substituted t-cumyl chloride (or bromide) in the presence of a suitable phenol catalyst to form a symmetrical dicumyl peroxide in a relatively non-aqueous system.

DETAILED DESCRIPTION OF THE INVENTION

The olefin is α-methylstyrene or a substituted α-methylstyrene where the substituents are inert groups substituted on the phenyl ring of the α-methylstyrene. Suitable substituents include lower alkyl groups of 1 to 6 carbons such as methyl, ethyl, propyl, isopropyl, butyl, t-butyl, amyl, t-amyl and hexyl, halo groups such as chloro, bromo and fluoro, ether groups such as methoxy, ethoxy, propoxy, isopropoxy and phenoxy and aryl groups such as phenyl and naphthyl.

The reactive halide is t-cumyl chloride (or bromide) or a substituted t-cumyl chloride (or bromide) where the substituents are inert groups substituted on the phenyl ring of the t-cumyl halide and the reactive halide is the addition product of hydrogen chloride or hydrogen bromide to the particular olefin employed.

The aqueous hydrogen peroxide solution can vary from about 25% to 98% and preferably should be 50–70%. Concentrations above 70% become hazardous to work with. As the concentration is decreased from 70%, the rate of reaction will decrease and more hydrolysis of the t-cumyl chloride will occur. Consequently, more phenol will have to be used to overcome this rate retarding effect of the water and/or more cumyl chloride will be required. From a commercial standpoint 70% hydrogen peroxide is most preferable. In any event water should not compose more than 20% of the reaction medium and preferably not more than 5–10%.

The phenol catalyst is phenol or naphthol or a substituted phenol or naphthol with an inert substituent such as alkyl groups of 1 to 6 carbons, alkoxy groups of 1 to 6 carbons, aryloxy groups of 6 to 10 carbons, halo groups such as chloro, bromo or fluoro or aryl groups of 6 to 10 carbons. Preferably the substituents should not be in the position ortho to the OH group where they would create steric hindrance to the OH group. 2,6-Disubstituted phenols are non-operable. For example, the hydroxyl group in 2,6-diisopropylphenol is too sterically hindered to generate any catalytic effect on the reaction. o-Cresol is not as effective as p-cresol. Strong electron withdrawing groups in the para position, such as chloro and bromo accelerate the reaction considerably. Some phenols are more soluble in the reaction mixture then others and are therefore more suitable.

The following is a list of suitable phenols and naphthols: phenol, ortho, meta and para cresols, chlorophenols, bromophenols, methoxyphenols, ethylphenols, isopropylphenols, para t-butylphenol, para phenylphenol, 3,4-dichlorophenol, 3,4-dimethylphenol, alpha-naphthol and beta-naphthol.

From a practical standpoint it is advantageous to use a cheap low molecular weight phenol which can be readily extracted out of the reaction mixture with aqueous caustic. Phenol and the meta and para cresols or mixtures thereof are especially suitable. Fused ring phenols such as naphthols are also suitable.

The reaction is run in the temperature range of 10°–50° C., preferably 20°–40° C. Since the phenol acts as a catalyst, the reaction temperature and reaction time are quite dependent on the amount of phenol added. When small amounts of phenol are added, the reaction will take longer and should be run at a higher temperature than when larger amounts of phenol are added.

The mole ratio of olefin (i.e. α-methylstyrene) to hydrogen peroxide may vary over a wide range from 0.5:1 to 5:1 or larger but from a practical standpoint it is advisable to use a mole ratio of 1.75:1 to 2.5:1. Dicumyl peroxide is still produced at the lower mole ratios but the yields are lower and the product is contaminated with cumene hydroperoxide.

The t-cumyl halide is charged in an amount of about 5–15 mole percent based on the olefin charged. Generally, one would use 7–10 mole percent. Increasing the mole percent t-cumyl halide increases the reaction rate but usually increases the amount of impurities generated as well.

The components of the feed may be charged to the reaction zone in any order. However, one should not leave the α-methylstyrene, t-cumyl halide and phenol in contact with each other for long periods of time or at high temperatures since the phenol catalyzes the oligomerization of the α-methylstyrene in the presence of the t-cumyl halide. It has been preferable to add the t-cumyl halide to a stirring mixture of the hydrogen peroxide, α-methylstyrene and phenol. The t-cumyl halide can be added neat or as a solution in the α-methylstyrene or even in an inert diluent. The addition of the t-cumyl halide should be carried out at such a rate and temperature that the reaction can be easily controlled. If the halide is added too fast at a high temperature in the presence of a considerable amount of phenol, a runaway reaction could occur. Addition of the hydrogen peroxide to a stirring solution of the α-methylstyrene, cumyl chloride and phenol at room temperature also works quite well.

The reaction time is dependent upon the temperature, the concentration of t-cumyl halide in the α-methylstyrene, the concentrations of phenol, the amount of water present in the system and the substitution of the phenol. The reactions can be readily monitored by gas chromatography or liquid chromatography to determine when the reaction is complete.

The product, dicumyl peroxides, are useful crosslinking agents for high and low density polyethylene, elastomers and rubbers.

EXAMPLES

The examples will demonstrate the preparation of dicumyl peroxides using the phenol catalyzed system and hydrogen peroxide, the effect of the reaction variables on the reaction time and yield, the ineffectiveness of the non-catalyzed system, and that some phenols are more effective catalysts than others. They will also demonstrate the continuous production of dicumyl peroxide using the process of this invention.

Most reactions were monitored by gas chromatography to determine the extent of reaction. The gas chromatography analyses were carried out on a Hewlett Packard 5710 A gas chromatograph coupled to a 3380 S integrator. An 18 inch ⅛ inch diameter 3% OV-17 column was used. The injection port temperature was 110° C. and the thermal detector temperature was 250° C. For dicumyl peroxide the column temperature was programmed at 8° C. per minute from 45° C. to 210° C. and the helium flow rate was approximately 90 cc per minute. The reaction mixture was diluted about 6:1 in pentane to flash the components through the injection port. A 0.25 minute delay was carried on the integrator so the pentane would not integrate. Final assays and yields in most cases were determined accurately by liquid chromatography using analytically pure standards and internal standards.

EXAMPLE I

Preparation of t-Cumyl Chloride

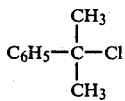

Aralkyl halides such as t-cumyl chloride can be prepared by a variety of chemical methods such as from aralkyl alcohols and hydrogen halide [see e.g. H. C. Brown, et al, Am. Chem. Soc. 79, 1897 (1957)] or by the free radical halogenation of an aralkane [see e.g. M. S. Kharasch and H. C. Brown, J. Am. Chem. Soc. 61, 2142 (1939)]. Below is described the method we used for preparing t-cumyl chloride:

Into a jacketed 2 liter reactor equipped with a thermometer, gas inlet tube, mechanical stirrer, bottom outlet and a water-cooled condenser connected to a gas bubbler, was added 708 grams (6 moles) α-methylstyrene. Hydrogen chloride was passed into the α-methylstyrene over 2½ hours at 27°-29° C. at a slow enough rate that complete absorption was obtained. After 226.3 grams (6.2 moles) of hydrogen chloride had been added, hydrogen chloride bubbled through the gas bubbler. The addition was stopped and the solution was stirred ½ hour at 28°-29° C. The product was drained into a tared glass bottle and weighed. The bottle was tightly capped and stored in the freezer compartment of a refrigerator. The product weighed 927 grams for a 100% yield.

Although it may be more practical on a commercial basis to prepare a solution of cumyl chloride in α-methylstyrene, it was found much easier on a laboratory scale to prepare 100% cumyl chloride and accurately add the desired amount to each reaction. It was much easier to obtain accurate concentrations of the t-cumyl chloride operating in this manner rather than trying to accurately weigh small amounts of hydrogen chloride into the reaction mixture each time.

EXAMPLE II

Preparation of Dicumyl Peroxide

This example demonstrates the difference between a phenol catalyzed reaction and a non-catalyzed reaction in the preparation of dicumyl peroxide from α-methylstyrene, cumyl chloride and hydrogen peroxide.

A. Phenol Catalyzed Reaction

Into a 200 ml jacketed reactor equipped with a mechanical stirrer, thermometer, water-cooled condenser and addition funnel were added 35.4 grams (0.3 m) α-methylstyrene, 3.8 grams (0.04 m) phenol and 4.9 grams (0.1 m) 70% hydrogen peroxide. The stirrer was activated and the temperature of the solution was adjusted to 24° C. by circulating water through the reactor jacket. The cumyl chloride, 3.1 grams (0.02 m) was transferred to the addition funnel and added dropwise to the rapidly stirred reaction mixture over 15 minutes while holding the temperature at 24° C. After the addition was complete, the reaction was stirred an additional ½ hour at 24°-25° C., the temperature raised to 30° C., the reaction stirred 2 hours at 30° C., the temperature raised to 35° C. and the reaction stirred 1 hour at 35° C. At this point, the gas chromatographic scans indicated the reaction was complete. The reaction was terminated by adding 25 mls of water, stirring 5 minutes, adding 50 mls of pentane, stirring an additional few minutes and separating the aqueous layer. The organic layer was washed with 25 mls of 15% sodium bisulfite, 25 mls of 15% NaOH, 50 mls of saturated sodium bicarbonate solution (twice) and 50 mls of water (3 times). The pentane solution was dried over anhydrous sodium sulfate, filtered and the pentane stripped off on a rotating evaporator under reduced pressure. The residual yellow liquid weighed 38.3 grams and assayed 55.1% dicumyl peroxide by liquid chromatography. This gave a 78.2% corrected yield based on the hydrogen peroxide. The volatiles were steam distilled out of the crude product under vacuum (see Example III). The organic residue after isolation and drying weighed 22.3 grams and assayed 89.6% by liquid chromatography.

B. Non-Catalyzed Reaction

Into a 250 ml round bottom flask equipped with a magnetic stirrer, condenser, thermometer and addition funnel were added 59.0 grams (B 0.05 m) α-methylstyrene and 9.8 grams (0.2 m) of 70% H₂O₂. The flask was immersed in a 25° C. water bath and the temperature allowed to come to 23° C. Then with rapid stirring, 6.2 grams (0.14 m) of cumyl chloride were added over 5 minutes. The reaction mixture was stirred vigorously for 35 minutes at 25° C.±2° C., the reaction temperature raised to 30° C. and stirred 1 hour at 30° C.±2° C., the reaction temperature raised to 35° C. and the reaction mixture stirred an additional hour at 35° C.±2° C., the reaction temperature raised to 40° C. and the reaction mixture stirred 1 hour at 40° C.±2° C. At this point there was essentially no dicumyl peroxide formed and about 5% cumene hydroperoxide formed. The reaction mixture was allowed to stand at room temperature over the weekend and then stirred an additional 2 hours at room temperature. The gas chromatography scans indicated there was still less than 1% dicumyl peroxide present and about 5% cumene hydroperoxide present. The reaction mixture was stirred with 15% NaOH, the organic layer separated and discarded in the organic waste bottle since it contained essentially no dicumyl peroxide.

EXAMPLE III

Steam Stripping of Dicumyl Peroxide

This example describes the procedure for steam distilling off the volatiles from the crude washed dicumyl peroxide and the isolation and drying of the final product.

The washed dicumyl peroxide was transferred to a 2 liter 3-neck flask equipped with a thermometer, steam inlet line, magnetic stirrer and distilling head connected to a condenser, receiver and dry ice trap connected to a manometer and vacuum pump. Approximately 400 mls of water were added to the flask, the magnetic stirrer activated and a vacuum of 100–120 mm Hg drawn on the system. Then the steam line was cracked open and the glass inlet lowered below the level of the liquid. The volatile components were steam distilled out of the flask and collected in the receiver and the dry ice trap. The temperature in the flask was held around 55°–60° C. throughout the steam distillation. The steam stripping required approximately 1½ hours at 55°–60° C. and 100–120 mm Hg. At the end of the steam stripping (no organic film in the condenser), the steam inlet was raised above the level of the liquid, the steam shut off and then the vacuum pump was turned off. The vacuum was released and the contents of the flask cooled to about 30° C. The mixture was transferred to a 2 liter separatory funnel and the stripped dicumyl peroxide taken up in 400 mls of pentane by shaking for 5 minutes. The pentane layer was separated, dried over anhydrous sodium sulfate, filtered and the pentane stripped off under reduced pressure on a rotating evaporator. A water aspirator was used to remove most of the pentane and the last traces were removed by stripping with a vacuum pump at 50° C. The residue was weighed and assayed by liquid chromatography using an internal standard.

EXAMPLE IV

Preparation of Dicumyl Peroxide at 30° C.

This example demonstrates that the reaction can be satisfactorily carried out at 30° C. and programming the reaction temperature is not necessary.

Into a 200 ml jacketed reactor equipped with a mechanical stirrer, thermometer, water-cooled condenser and addition funnel were added 53.2 grams (0.45 m) a-methylstyrene, 7.6 grams (0.08 m) phenol and 9.8 grams (0.2 m) of 70% hydrogen peroxide. The stirrer was activated and the temperature of the solution was adjusted to 29°–30° C. by circulating warm water through the reactor jacket. The cumyl chloride, 6.2 grams (0.04 m), was added dropwise from the addition funnel over 15 minutes while holding the reaction temperature at 30° C. After the addition was complete, the reaction was stirred for 1¼ hours at 30° C. at which point the gas chromatographic scans indicated the reaction was complete. The reactions were terminated at this point by the addition of 50 mls of water, the mixture stirred 15 minutes and 10 mls of 50% NaOH added, the mixture stirred an additional 15 minutes and the aqueous layer separated. The organic layer was washed with 50 ml portions of 15% NaOH, water, saturated sodium bicarbonate solution and water until neutral. The organic layer was diluted with 50 mls of pentane, dried over anhydrous sodium sulfate, filtered and the pentane stripped off on a rotating evaporator under pressure. The residual yellow liquid weighed 59.4 grams and assayed 70.7% dicumyl peroxide by liquid chromatography for a 77.6% corrected yield based on the hydrogen peroxide. Agter steam stripping off the volatiles the dicumyl peroxide assayed 90.4%.

EXAMPLE V

Preparation of Dicumyl Peroxide Using 50% Hydrogen Peroxide

This example demonstrates that the process works with 50% hydrogen peroxide. The reaction is slower and more t-cumyl chloride is required due to partial hydrolysis of the cumyl chloride by the water in the hydrogen peroxide.

The reaction was started in the same manner as the reactions in Example IV except 13.6 grams (0.2 m) of 50% hydrogen peroxide were used instead of the 70% hydrogen peroxide. The reaction was stirred 2 hours at 30° C. after the cumyl chloride addition was complete. At this point, the gas chromatographic scans indicated that most of the cumyl chloride had hydrolyzed to cumyl alcohol and the reaction had stopped. An additional 6.2 grams (0.04 m) of cumyl chloride were added over 5 minutes and the reaction stirred an additional 1¼ hours at 30° C. The reaction was terminated at this point by the addition of 50 mls of water. The reaction was worked up in the same manner as in Example IV. The crude product weighed 64.5 grams and assayed 65.1% dicumyl peroxide by liquid chromatography for a 77.6% corrected yield based on the hydrogen peroxide. After steam stripping off the volatiles, the dicumyl peroxide assayed 89.9%.

EXAMPLE VI

Preparation of Dicumyl Peroxide Using Liquified Phenol

This example demonstrates that the process is operable with liquified phenol (contains about 9% water to liquify the phenol) and the reaction rate is comparable provided enough phenol is added to overcome the rate retarding effect of the water.

The reaction was run in the same manner as the reaction in Example IV except 9.8 grams (0.093 m) of liquified phenol ($v$91% phenol, 9% $H_2O$) were used instead of the solid anhydrous phenol. After the cumyl chloride addition was complete, the reaction had to be stirred an additional 1½ hours at 30° C. to complete the reaction. The reaction was terminated and worked up using the same procedure described in Example IV. The crude product weighed 59.0 grams and assayed 72.5% dicumyl peroxide by liquid chromatography for a 79.6% corrected yield based on the hydrogen peroxide. After steam stripping off the volatiles, the dicumyl peroxide assayed 91.5%.

EXAMPLE VII

Preparation of Dicumyl Peroxide

Varying the Mole Ratio of α-Methylstyrene to 70% Hydrogen Peroxide

This example demonstrates the effect on the reaction time and the yield of dicumyl peroxide when the mole ratio of α-methylstyrene to 70% hydrogen peroxide is varied from 3:1 to 1:1.

These experiments were run essentially the same as Example IV except the initial reaction temperature was 25° C. and the amount of α-methylstyrene was varied. The cumyl chloride was added to the stirred mixture of α-methylstyrene, phenol and 70% hydrogen peroxide over 15 minutes at 25° C. After the addition was complete, the reaction was stirred an additional ½ hour at 25° C., the temperature raised to 30° C., the reaction stirred 1½ hours at 30° C. (if necessary), the temperature raised to 35° C. or 40° C. and the reaction completed. The reactions were monitored by gas chromatography. The reactions were worked up in the same manner as described in Example IV.

When the reaction was run using a 1:1 mole ratio of α-methylstyrene to hydrogen peroxide, the reaction was very exothermic during the addition of the cumyl chloride and about two thirds of the way through the addition an uncontrollable exotherm occurred and the reaction mixture spewed out of the reactor. The reaction was repeated using one half as much cumyl chloride and phenol. Under these conditions, the reaction was controllable but a low yield of dicumyl peroxide was obtained and a considerable amount of cumene hydroperoxide was generated. The results are summarized in Table I.

Table I

Effect of Mole Ratio of α-Methylstyrene to 70% $H_2O_2$ on Reaction Time and Dicumyl Peroxide Yield

| Exp't# | Moles α-Methyl-styrene | Moles 70% $H_2O_2$ | Mole Ratio | Moles Cumyl Chloride | Moles Phenol | Reaction Time hrs. | Crude Yield g. | Crude Assay % | Corr. Yield g. | Corr. Yield % |
|---|---|---|---|---|---|---|---|---|---|---|
| 1 | 0.6 | 0.2 | 3:1 | 0.04 | 0.08 | 3½ | 76.6 | 55.1 | 42.2 | 78.2 |
| 2 | 0.5 | 0.2 | 2.5:1 | 0.04 | 0.08 | 2¼ | 66.5 | 65.6 | 43.6 | 80.8 |
| 3 | 0.45 | 0.2 | 2.25:1 | 0.04 | 0.08 | 1½ | 59.1 | 70.6 | 41.8 | 77.4 |
| 4 | 0.4 | 0.2 | 2:1 | 0.04 | 0.08 | 1¾ | 51.7 | 74.9 | 38.7 | 71.7 |
| 5 | 0.2 | 0.2 | 1:1 | 0.04 | 0.08 | Decomposition during addition of t-cumyl chloride | | | | |
| 6 | 0.2 | 0.2 | 1:1 | 0.02 | 0.04 | ½ | 20.8 | 79.4 | 16.5 | 30.5 |

EXAMPLE VIII

Preparation of Dicumyl Peroxide Using Various Amounts of Phenol and Cumyl Chloride This example demonstrates how varying the amount of phenol catalyst and cumyl chloride effect the reaction time required to complete the reaction, the yield of dicumyl peroxide and the assay of the steam stripped product.

These experiments were run essentially the same as in Example IV except the amount of phenol and cumyl chloride were varied from reaction to reaction. The cumyl chloride was added over 15 minutes at approximately 30° C. After the addition was complete, the reaction was stirred at 30° C. until the gas chromatographic scans indicated the reaction was complete. The reactions were worked up in the same manner as described in Example IV. The results are summarized in Table II.

matographic scans indicate the reaction is complete. This example also demonstrates that the assay of the steam stripped product is not effected by running the reaction beyond this point.

Into a two liter jacketed reactor equipped with a mechanical stirrer, thermometer, water-cooled condenser and addition funnel were added 425.6 grams (3.6 m) α-methylstyrene, 60.8 grams (0.65 m) phenol and 78.4 grams (1.6 m) 70% hydrogen peroxide. The stirrer was activated and the temperature of the reactor contents adjusted to 27° C. by circulating water through the reactor jacket. The cumyl chloride, 49.6 grams (0.32 m), was transferred to the addition funnel and added dropwise to the rapidly stirred reaction mixture over 15 minutes while holding the temperature at 27°–31° C. After the addition was complete, the reaction was stirred an additional 2 hours at 30° C. Samples were taken during the reaction product by allowing 110–115 mls of the stirring reaction mass to drain into tared beakers at specific intervals. The samples were weighed, the reaction terminated and the product worked up using the procedure described in Example IV. The results are summarized in Table III.

Table III

Effect of Reaction Time on Dicumyl Peroxide Yield and Assay

| Sample# | Reaction Time hrs. | Sample Weight g. | Crude Yield g. | Crude Assay % | Corrected Yield % | Steam Stripped Assay % |
|---|---|---|---|---|---|---|
| 1 | ½ | 110 | 82.6 | 62.3 | 65.3 | 90.9 |
| 2 | ¾ | 105.8 | 82.0 | 67.2 | 72.7 | 92.5 |
| 3* | 1 | 100.6 | 78.0 | 69.8 | 75.5 | 91.9 |
| 4 | 1¼ | 110.5 | 86.0 | 70.1 | 76.1 | 92.8 |
| 5 | 2 | 90 | 70.7 | 72.4 | 77.9 | 93.0 |
| 6 | 2 | 87 | 67.7 | 79.5 | 79.2 | 91.8 |

*Gas chromatographic scan indicated reaction was complete.

Table II

Effect of Varying the Amount of Phenol and Cumyl Chloride on Reaction Time and Dicumyl Peroxide Yield

| Exp't# | Moles α-Methyl-styrene | Moles 70% $H_2O_2$ | Moles Cumyl Chloride | Moles Phenol | Reaction Time hrs. | Crude Yield g | Crude Assay % | Corr. Yield % | Steam Stripped Assay % |
|---|---|---|---|---|---|---|---|---|---|
| 1 | 0.45 | 0.2 | 0.032 | 0.064 | 4 | 57.9 | 70.8 | 75.8 | 92.0 |
| 2 | 0.45 | 0.2 | 0.032 | 0.08 | 2 | 58.5 | 70.6 | 76.3 | 92.0 |
| 3 | 0.45 | 0.2 | 0.032 | 0.096 | 1¼ | 59.7 | 70.0 | 77.2 | 91.6 |
| 4 | 0.45 | 0.2 | 0.04 | 0.064 | 2½ | 59.8 | 68.9 | 75.8 | 91.9 |
| 5 | 0.45 | 0.2 | 0.04 | 0.08 | 1¼ | 59.4 | 70.7 | 77.6 | 90.4 |
| 6 | 0.45 | 0.2 | 0.04 | 0.096 | ¾ | 60.6 | 68.8 | 77.1 | 89.8 |
| 7 | 0.45 | 0.2 | 0.048 | 0.064 | 1¼ | 60.9 | 65.8 | 74.1 | 90.6 |
| 8 | 0.45 | 0.2 | 0.048 | 0.08 | 1 | 61.8 | 68.9 | 78.7 | 90.8 |
| 9 | 0.45 | 0.2 | 0.048 | 0.096 | 0.67 | 61.7 | 69.5 | 79.3 | 91.5 |

EXAMPLE IX

Effect of Reaction Time on the Dicumyl Peroxide Yield and Assay

This example demonstrates that the yield of dicumyl peroxide increases with time up to a point and then levels off. This is the same point at which the gas chro-

EXAMPLE X

Preparation of Dicumyl Peroxide Using A Reverse Addition of Reagents

This example demonstrates the effect of adding the hydrogen peroxide to a solution of the α-methylstyrene, cumyl chloride and phenol.

Into a 200 ml jacketed reactor equipped with a mechanical stirrer, thermometer, water-cooled condenser and addition funnel were added in the following order, 53.2 grams (0.45 m) α-methylstyrene, 7.6 grams (0.08 m) phenol and 6.2 grams (0.04 m) t-cumyl chloride. The reaction temperature was adjusted to 39° C. by circulating warm water through the reactor jacket. To the stirred solution was added 9.8 grams (0.2 m) 70% hydrogen peroxide dropwise from the addition funnel over 5 minutes while holding the reaction temperature at 30° C. After the addition was complete, the reaction was stirred at 30° C. for 1¼ hours at which point the gas chromatographic scans indicated the reaction was complete. The reaction was terminated and worked up using the procedure described in example IV. The crude unstripped product weighed 59.8 grams and assayed 70.8% by liquid chromatography for a 78.3% yield. The crude product was almost colorless. The steam stripped product assayed 91.4%.

EXAMPLE XI

Preparation of Dicumyl Peroxide Using Various Phenols as Catalysts

This example demonstrates that phenols (including naphthols) containing substituents also are effective catalysts for the process of this disclosure. Some work better than others depending upon the nature and position of the substituent and the solubility of the phenol in the reaction medium. The reactions were monitored by gas chromatography to determine when the reactions were complete.

The following general procedure was used for the preparation of the dicumyl peroxide, substituting an equimolar amount of the desired phenol in each case. Into a 200 ml jacketed reactor equipped with a mechanical stirrer, thermometer, water-cooled condenser and addition funnel was added 53.2 grams (0.45 m) α-methylstyrene. The stirrer was activated and 0.08 mole of the desired phenol was added to the reactor followed by 9.8 grams (0.2 m) of 70% hydrogen peroxide. The reaction temperature was adjusted to 30° C. by circulating warm water through the reactor jacket. The cumyl chloride, 6.2 grams (0.04 m), was added dropwise from the addition funnel over 15 minutes while holding the reaction temperature at 30° C. After the addition was complete, the reaction was stirred at 30° C. (in most cases) until the gas chromatographic scans indicated the reaction was complete. In most cases the reactions were worked up using the procedure described in Example IV. If the phenol was not removed in the aqueous caustic wash, the organic layer was washed twice for 10 minute periods with 30 mls of methanolic caustic (3 parts by volume methanol and 1 part 50% NaOH). The results are summarized in Table IV.

Table IV

| | | Preparation of Dicumyl Peroxide Using Various Phenols as Catalysts | | | | | | |
|---|---|---|---|---|---|---|---|---|
| Exp't# | Phenol Catalyst | Reaction Time Hrs. @30° C. | @35° C. | @40° C. | Methanolic Caustic Wash Required | Crude Yield g. | Crude Assay % | Corr. Yield % | Steam Stripped Assay % |
| 1 | o-Cresol | 2 | 1 | — | No | 58.2 | 61.6 | 66.3 | 91.5 |
| 2 | 2,6-Diisopropyl-phenol | 2 | 1 | 1 | Yes | 42.3 | ~2.5 | ~2 | — |
| 3 | 4-t-Butylphenol | 2 | ½ | — | No | 57.0 | 71.3 | 75.1 | 92.7 |
| 4 | 4-Chlorophenol | ¾ | — | — | No | 57.5 | 68.5 | 72.8 | 87.6 |
| 5 | 2-t-Butylphenol | 2 | 1 | 2 | Yes | 47.2 | 42.6 | 37.2 | 92.5 |
| 6 | 2-Naphthol | 2 | 1 | — | No | 56.4 | 67.5 | 70.4 | 91.2 |
| 7 | 3-Methoxyphenol | 2 | 1¼ | 1 | Yes | 40.5 | 76.9 | 57.6 | 93.4 |
| 8 | 4-Bromophenol | ¾ | — | — | No | 58.1 | 68.8 | 73.9 | 87.3 |
| 9 | 4-Methoxyphenol | 2 | — | — | Yes | 59.0 | 68.4 | 74.6 | 90.7 |
| 10 | Phenol | 1¼ | — | — | No | 59.4 | 70.7 | 77.6 | 90.4 |

EXAMPLE XII

This example demonstrates the continuous preparation of dicumyl peroxide from α-methylstyrene, cumyl chloride, phenol and 70% hydrogen peroxide.

A series of 4 jacketed reactors containing bottom outlets were set up in a series in such a way that the contents of the reactors would flow from one reactor to the other. The first three reactors had a 700 ml capacity and the fourth reactor had a 1000 ml capacity. Each reactor was equipped with a thermometer and a 4-blade glass stirrer connected to a mechanical stirrer. Water was pumped through the reactor jackets by Little Giant pumps from thermostatted baths. Calibrated metering pumps were used to pump the reagents from reservoirs into the first reactor ($R_1$) and varistaltic pumps were used to transfer the reaction mixture from the first reactor to the second reactor ($R_2$) and from the second reactor to the third reactor when the volume reached a preset level.

The reaction was initiated as a batch type reaction in $R_1$. The desired amounts of α-methylstyrene, cumyl chloride and phenol were added to $R_1$, the stirrer activated and the 70% hydrogen peroxide added over 15 minutes from a dropping funnel while controlling the reaction temperature in the desired temperature range by pumping warm water through the reactor jacket. Upon completion of the hydrogen peroxide addition, the metering pumps and the varistaltic pumps were activated and the continuous portion of the run begun. The reaction mixture was pumped out of $R_1$ into $R_2$ at such a rate as to maintain a constant volume in $R_1$. When the volume in $R_2$ built up to a volume equal to the volume in $R_1$, it was transferred by a varistaltic pump into $R_3$ at such a rate that the volume in $R_2$ remained equal to that in $R_1$. Water was metered into $R_3$ at a constant rate and mixed with the reaction mixture until the volume built up to a volume equal to that in $R_2$ (30 minutes) whereupon it overflowed into $R_4$ where 50% sodium hydroxide was metered in at such a rate as to maintain a 15% sodium hydroxide concentration in the aqueous phase. After 30 minutes the volume in $R_4$ was great enough that it overflowed into a separator. After the volume in the separator had built up sufficiently, the bottom aqueous caustic layer and the top organic layer were continuously drawn off into separate containers.

The composite organic layer was washed to neutral, dried over anhydrous sodium sulfate, filtered and analyzed by liquid chromatography. A portion of the crude dicumyl peroxide was steam stripped as in Example III and assayed by liquid chromatography.

Procedure

A solution of 110.5 grams of cumyl chloride in 854.8 grams of α-methylstyrene was prepared and charged to a 1000 ml reservoir. A solution of 200 grams of 70% hydrogen peroxide was charged to a 500 ml reservoir and 175 grams of liquified phenol (90%) was charged to a 250 ml reservoir. All the reservoirs were individually connected to metering pumps. To the first reactor was added 197.3 grams of α-methylstyrene and 36.8 grams of liquified phenol. The temperature in $R_1$ was adjusted to 27° C. by circulating warm water through the jacket. To this solution was added 25.5 grams of t-cumyl chloride and then 36.8 grams of 70% hydrogen peroxide were added dropwise from a dropping funnel over 15 minutes. The temperature in $R_1$ was allowed to rise to 35° C.±1° C. during this period. The temperature was controlled at 35° C. throughout the remainder of the run by circulating 30° C. water through the reactor jacket. At the end of the hydrogen peroxide addition the metering pumps and varistaltic pumps were activated. The α-methylstyrene-cumyl chloride solution was pumped into $R_1$ at a rate of 5.094 grams/minute. The 70% hydrogen peroxide solution as pumped into $R_1$ at a rate of 0.839 grams/minute and the liquified phenol was pumped in at a rate of 0.804 grams/minute.

As the volume in $R_1$ began to increase, a varistaltic pump transferred the reaction mixture from $R_1$ to $R_2$ at such a rate as to keep the volume constant in $R_1$. The temperature in $R_2$ was raised to 45° C.±1° C. by circulating 45° C. water through the jacket of $R_2$. After the metering pumps had been running 45 minutes, the volume in $R_2$ was equal to the volume in $R_1$ and the reaction mixture was pumped out of $R_2$ into $R_3$ at a rate equal to the rate of the reaction mixture being pumped into $R_2$. At the same time the water metering pump was activated and water was metered into $R_3$ at a rate of 4.442 mls/minute. The temperature in $R_3$ was maintained at 45° C. by circulating 50° C. water through the reactor jacket. One half hour later the hydrolyzed mixture in $R_3$ had built up to a sufficient volume that it began to transfer into $R_4$. At that point the 50% sodium hydroxide metering pump was activated and 50% sodium hydroxide was pumped into $R_4$ at a rate of 0.929 mls/minute. The temperature in $R_4$ was maintained at 50° C. by circulating 50° C. water through the reactor jacket. One half hour later the strongly basic mixture was drained out of the bottom of $R_4$ into a separator at such a rate as to keep the volume in $R_4$ approximately constant. As the volume in the separator built up, the basic aqueous layer was slowly drained into one container and the top organic layer was drawn off into another container.

After 3 hours of operation, the metering pumps to $R_1$ were shut down. After another 45 minutes $R_1$ was empty and the varistaltic transfer pump from $R_1$ to $R_2$ was shut off. After the contents of $R_2$ had completely transferred to $R_3$, the water metering pump was shut off. After the contents of $R_3$ had completely transferred to $R_4$, the 50% sodium hydroxide metering pump was shut off. After the contents of $R_4$ had completely drained into the separator and had been separated, the aqueous caustic layer in the one container was set aside for neutralization and waste disposal. The organic layer in the other container was transferred to a 3 liter reactor and washed successively with 200 mls of 15% sodium hydroxide, 1000 l mls water, 500 mls of saturated sodium bicarbonate solution, two portions of 250 mls of water and two portions of 250 mls of saturated sodium chloride solution. The crude product weighed 1076.5 grams and assayed 61.2% by liquid chromatography. This calculated out to a 63% yield based on the hydrogen peroxide used.

A 60 gram sample of the crude material was steam stripped using the procedure described in Example III. The steam stripped sample assayed 90.0% by liquid chromatography.

At the completion of the workup the reservoirs were emptied and the contents weighed to determine the exact amount of reagents used. There was 48.3 grams of the α-methylstyrene-cumyl chloride solution, 48.9 grams of 70% hydrogen peroxide and 30.2 grams of phenol remaining. The actual amounts of reagents consumed and the corrected pumping rates were then determined. The following table summarizes the amounts of reagents used, the mole ratio of reagents to hydrogen peroxide and the pumping rate of the metering pumps.

In summary, $R_1$, the initial reactor was run at 35° C. with a 45 minute residence time. $R_2$, the finishing reactor was run at 45° C.±1° C. with a 30 minute residence time. $R_4$, the sodium hydroxide wash tank was run at 50° C. with a 30 minute residence time. The reaction was monitored by gas chromatography and the area % VPC assay of the dicumyl peroxide held around 43% in $R_1$ during the continuous addition of the reagents and held around 57 ½% in $R_2$. The area % increased to 68% in the container holding the organic layer after the separation.

| Chemicals | Total Weight or Volume Used | Mole Ratio to $H_2O_2$ | Pumping Rate |
|---|---|---|---|
| 70% $H_2O_2$ | 187.9 g | 1:1 | 0.839 g/min |
| α-methylstyrene | 1009.3 g | 2.21:1 | — |
| cumyl chloride | 130.5 g | .22:1 | — |
| α-methylstyrene-cumyl chloride solution | 1139.8 g | — | 5.094 g/min |
| 90% phenol | 181.6 g | 0.45:1 | 0.804 g/min |
| $H_2O$ | 955 ml | — | 4.442 mls/min |
| 50% NaOH | 195 mls | 0.95:1 | 0.929 mls/min |

Thus, having described the invention, what is claimed is:

1. A process for preparing symmetrical dicumyl peroxides which process consists essentially of:
    (a) reacting an olefin, a reactive organic halide and aqueous hydrogen peroxide under relatively non-aqueous conditions in the absence of a free acid and in the presence of a phenol catalyst at a temperature in the range of 10°–50° C. where,
    (b) said olefin is α-methylstyrene or a substituted alpha-methylstyrene where the substituents are inert groups substituted on the phenyl ring of the alpha-methylstyrene and is selected from alkyl of 1 to 6 carbons, Cl-, Br-, F-, aryl of 6 to 12 carbons, alkoxy of 1 to 5 carbons or aryloxy of 7 to 10 carbons,
(c) said reactive halide is t-cumyl chloride or t-cumyl bromide or a substituted t-cumyl chloride or t-cumyl bromide where the substituents are inert groups substituted on the phenyl ring of the t-cumyl halide and the reactive halide is the addition product of hydrogen chloride or hydrogen bromide to the particular olefin employed,
(d) said aqueous hydrogen peroxide is an aqueous solution containing from about 25% to 98% hydrogen peroxide and such that the total amount of water in the reaction system is not above 20%,
(e) said phenol catalyst is phenol or naphthol, a mono substituted phenol or naphthol or a di or tri substituted phenol or naphthol where the phenol or naphthol is not substituted simultaneously in the 2 and 6 positions where the substituents are inert groups selected from alkyl of 1 to 6 carbons, alkoxy of 1 to 6 carbons, aryloxy of 6 to 10 carbons, Cl-, Br-, F-, or aryl of 6 to 10 carbons,
(f) the mole ratio of olefin to hydrogen peroxide is in the range 0.5:1 to 5:1 and,
(g) the reactive halide is charged in an amount of about 5–15 mole percent based on the olefin charged.

2. The process of claim 2 wherein the phenol catalyst is selected from o-cresol, 4-t-butylphenol, 4-chlorophenol, 4-bromophenol, 4-methyloxyphenol, beta-naphthol, 2-t-butylphenol, 4-phenylphenol, 3-methoxyphenol or phenol.

3. The process of claim 1 wherein the mole ratio of olefin to hydrogen peroxide is in the range of 1.75:1 to 2.5:1.

4. The process of claim 1 wherein the aqueous hydrogen peroxide is 45–75% hydrogen peroxide.

5. The process of claim 1 wherein the reaction temperature is maintained between 20° and 40° C.

* * * * *